US011092524B2

(12) United States Patent
Li et al.

(10) Patent No.: US 11,092,524 B2
(45) Date of Patent: Aug. 17, 2021

(54) METHOD AND DEVICE FOR PREPARING KARST CAVES BASED ON 3D PRINTING TECHNOLOGY

(71) Applicant: SHANDONG UNIVERSITY, Shandong (CN)

(72) Inventors: Shucai Li, Shandong (CN); Zhenhao Xu, Shandong (CN); Bin Gao, Shandong (CN); Xintong Wang, Shandong (CN); Wenyang Wang, Shandong (CN); Yuchao Du, Shandong (CN); Xin Huang, Shandong (CN); Dongdong Pan, Shandong (CN); Peng Lin, Shandong (CN)

(73) Assignee: SHANDONG UNIVERSITY, Jinan (CN)

(*) Notice: Subject to any disclaimer, the term of this patent is extended or adjusted under 35 U.S.C. 154(b) by 327 days.

(21) Appl. No.: 16/314,491

(22) PCT Filed: Jan. 10, 2018

(86) PCT No.: PCT/CN2018/072076
§ 371 (c)(1),
(2) Date: Dec. 31, 2018

(87) PCT Pub. No.: WO2018/209990
PCT Pub. Date: Nov. 22, 2018

(65) Prior Publication Data

US 2019/0204191 A1 Jul. 4, 2019

(30) Foreign Application Priority Data

May 16, 2017 (CN) ........................ 201710343216.1

(51) Int. Cl.
*B33Y 50/00* (2015.01)
*G01N 1/44* (2006.01)
(Continued)

(52) U.S. Cl.
CPC ................ *G01N 1/44* (2013.01); *B28B 1/14* (2013.01); *B28B 7/342* (2013.01); *B28B 11/24* (2013.01);
(Continued)

(58) Field of Classification Search
CPC ................................. G01N 1/44; B33Y 10/00
See application file for complete search history.

(56) References Cited

U.S. PATENT DOCUMENTS 10,809,175 B1 * 10/2020 Ayadat ............... G01N 15/0806
2007/0255501 A1 * 11/2007 Kellogg .................. G01V 1/28
702/16

(Continued)

FOREIGN PATENT DOCUMENTS

CN 103837390 A 6/2014
CN 104034563 A 9/2014

(Continued)

OTHER PUBLICATIONS

Mar. 28, 2018 Translation of International Search Report issued in International Patent Application No. PCT/CN2018/072076.

(Continued)

*Primary Examiner* — Leith S Shafi
*Assistant Examiner* — Nicholas R Krasnow
(74) *Attorney, Agent, or Firm* — Oliff PLC

(57) ABSTRACT

A method and device for preparing karst caves based on 3D printing technology. The method includes the following steps: determining size of a sample according to test requirements, constructing a 3D karst cave digital model based on three-dimensional karst cave scanning result, and carrying out 3D printing by using alloy to form primary karst cave sample; preparing rock similar material mixture according to proportioning scheme; pouring mixture into sample mold while burying karst cave model into mixture according to
(Continued)

Prepare low melting point alloy
Draw a three-dimensional karst cave digital model
Print a 3D karst cave model
Prepare similar materials of a rock test block
Bury the karst cave model into the rock materials
Remove a mold, cure, and mold at a low temperature
Brake the rock test block, and divert the alloy material
Recover the melted alloy material flowing out
Form a karst cave rock sample position of a karst cave; curing sample together with mold at room temperature until rock similar materials get hardened, removing mold, curing formed karst cave rock sample at constant temperature and constant humidity and then baking or heating same by electrifying heating wire in alloy to form rock sample with hollow karst cave; and filling hollow karst cave with different fillings to form different type of karst cave sample.

6 Claims, 2 Drawing Sheets

(51) Int. Cl.

| | |
|---|---|
| ***G01V 99/00*** | (2009.01) |
| ***G01N 1/36*** | (2006.01) |
| ***B33Y 10/00*** | (2015.01) |
| ***B28B 1/14*** | (2006.01) |
| ***B28B 11/24*** | (2006.01) |
| ***B33Y 50/02*** | (2015.01) |
| ***B28B 7/34*** | (2006.01) |
| ***G01N 1/28*** | (2006.01) |
| ***G01N 33/00*** | (2006.01) |
| ***E02D 1/02*** | (2006.01) |
| *B33Y 70/00* | (2020.01) |

(52) U.S. Cl.

CPC ............... *B33Y 10/00* (2014.12); *B33Y 50/02* (2014.12); *E02D 1/027* (2013.01); *G01N 1/2806* (2013.01); *G01N 1/36* (2013.01); *G01N 33/00* (2013.01); *G01V 99/005* (2013.01); *B33Y 70/00* (2014.12); *G01N 2001/366* (2013.01)

(56) References Cited

U.S. PATENT DOCUMENTS

| | | | | |
|---|---|---|---|---|
| 2015/0355158 | A1 | 12/2015 | Lander et al. | |
| 2020/0341159 | A1* | 10/2020 | Le Calvez | G01V 1/282 |
| 2020/0370423 | A1* | 11/2020 | Li | G05B 13/027 |
| 2021/0033515 | A1* | 2/2021 | Schimmel | G01N 15/08 |

FOREIGN PATENT DOCUMENTS

| | | | | |
|---|---|---|---|---|
| CN | 104515696 | A | | 4/2015 |
| CN | 104807685 | A | | 7/2015 |
| CN | 105034139 | A | | 11/2015 |
| CN | 105203359 | A | | 12/2015 |
| CN | 104196012 | B | * | 1/2016 |
| CN | 105628470 | A | | 6/2016 |
| CN | 105651570 | A | | 6/2016 |
| CN | 105651571 | A | | 6/2016 |
| CN | 105651572 | A | | 6/2016 |
| CN | 107084868 | A | | 8/2017 |
| WO | 2008/056170 | A1 | | 5/2008 |
| WO | 2011/070248 | A1 | | 6/2011 |

OTHER PUBLICATIONS

Mar. 28, 2018 International Search Report issued in International Patent Application No. PCT/CN2018/072076.

* cited by examiner

METHOD AND DEVICE FOR PREPARING KARST CAVES BASED ON 3D PRINTING TECHNOLOGY

FIELD OF THE INVENTION

The present invention relates to the technical field about civil engineering experiments, and specifically relates to a method and device for preparing karst caves based on 3D printing technology.

BACKGROUND OF THE INVENTION

With the urgent need for the construction of railways and highways at home and abroad, increasing railways are being built in the southwest of China. Karst caves are widely distributed in the southwest of China, so karst caves have become a common geological disaster in the construction of railway and highway projects. The existence of karst caves in the rock mass destroys the integrity and continuity of the rock mass itself, so that the strength of the rock mass is greatly reduced. At the same time, the strength, stress distribution and deformation characteristics of the rock mass are obviously different due to different geometrical shapes, filling properties and spatial distribution rules of the karst caves. Therefore, it is urgent to carry out and strengthen basic studies on the mechanical properties and failure mechanism of the rock mass reserves of the karst caves. At present, domestic and foreign scholars have conducted thorough work on the numerical simulation of geological disasters such as karst caves, but made a few experimental studies on karst caves. This is because karst caves, as a special structure, often develop into irregular shapes, and some karst caves are filled with certain substances therein. There is no relatively perfect preparation method.

At present, karst caves prepared in the experiments are faced up with the following problems that karst caves cannot be positioned accurately; precision control on karst cave dimensions is insufficient; the spatial shapes of karst caves cannot be fully considered; the karst caves are prepared by hollowing rock test blocks after formation thereof; and the prepared karst caves are greatly different from natural karst caves, etc.

In model test, there is no good preparation method for filled karst caves, so a relatively perfect method for preparing a karst cave rock sample is urgently needed.

SUMMARY OF THE INVENTION

In order to solve the above problems, the present invention provides a method and device for preparing karst caves based on 3D printing technology.

In order to achieve above objectives, the present invention adopts the following technical solutions:

A method for preparing karst caves based on 3D printing technology comprises the following steps:

(1) determining the size of a sample according to test requirements, constructing a 3D karst cave digital model based on a 3D karst cave scanning result, and carrying out 3D printing by using an alloy to form a primary karst cave sample;

(2) determining a proportioning scheme of an aggregate and a cementing material of a rock model according to the geometric similarity ratio, strength similarity ratio and elastic modulus similarity ratio of the rock sample to the model, and preparing a rock similar material mixture according to the proportioning scheme;

(3) pouring the mixture into a sample mold while burying the karst cave model into the mixture according to the position of a karst cave;

(4) curing the sample together with the mold at room temperature until the rock similar materials get hardened, removing the mold, curing the formed karst cave rock sample at a constant temperature and humidity and then baking the same or heating the same by electrifying a heating wire in the alloy to form a rock sample with a hollow karst cave;

(5) filling the hollow karst cave with different fillings to form a different type of karst cave sample.

In step (1), a low-melting-point metallic synthetic alloy is used.

In step (3), rock similar materials are weighed according to a proportion and uniformly mixed. The mixture is poured into the sample mold layer by layer while the karst cave model is buried into the mixture according to the position of a karst cave, with diversion holes being reserved. The interior of the mold is coated with a release agent, and vibration molding is carried out.

In step (3), the diversion holes are obtained from pre-buried small low-melting-point alloy strips communicating with the karst cave and the outside. After the alloy strips are melted, the alloy melt flows out to form the diversion holes.

In step (4), the sample is cured together with the mold at room temperature for a period of time until the rock similar materials get hardened. The mold is removed, and the formed karst cave rock sample is cured in a temperature- and humidity-constant curing box for a set period of time.

In step (4), the curing temperature is 20-25° C., and the curing relative humidity is higher than 94%.

In step (4), the formed test sample is baked or heated by electrifying the preset heating wire in the alloy. The karst cave made of the low-melting-point alloy and the alloy strips are fully melted. The alloy material flowing out after the karst cave is melted is recovered by virtue of the division holes of the sample during baking or electrifying, and a rock test block with a hollow karst cave is obtained.

In step (5), the preparation method of the muddy particle karst cave is that, after the set portion is printed in the karst cave printing process, the printed portion has an opening, through which the fillings are poured into the karst cave. The karst cave is further printed till the printing is completed, and the fillings are sealed in the karst cave.

In step (5), the specific method for preparing a water-filled karst cave is to fill the karst cave with water through the diversion holes after the preparation of the karst cave rock mass, and the water filling pressure is adjusted according to the experimental requirements to obtain a water-filled karst cave with different water pressures.

A preparation device using the above method comprises an oven, wherein an alloy recovery component is arranged at the bottom of the oven, and a constant-temperature and constant-humidity curing box and a water-filling pressure device are arranged outside the oven.

Compared with prior art, the present invention has the following beneficial effects:

(1) the present invention ensures the natural similarity of the karst cave model, and facilitates the adjustment on the shape, filling degree and the like of the karst cave to satisfy the actual engineering rock condition;

(2) the present invention can simulate the initial forms of various karst caves of different shapes and different sizes, and therefore has the advantage of a wide application range;

(3) the present invention can be widely applied to research on geological disasters containing karst caves in the fields of hydroelectricity, transportation, mines, etc., and therefore has a wide application range;

(4) the present invention is environment-friendly and pollution-free, and the karst cave generation materials can be recycled for the next time; and (5) the present invention adopts 3D printing to prepare samples, which simplifies the preparation steps, saves time and labor, and greatly reduces the cost.

BRIEF DESCRIPTION OF THE DRAWINGS

The accompanying drawings constituting a part of the present application are used for further understanding the present application, and the schematic embodiments of the present application and the description thereof are used for interpreting the present application, rather than constituting improper limitation to the present application.

Figure 1:
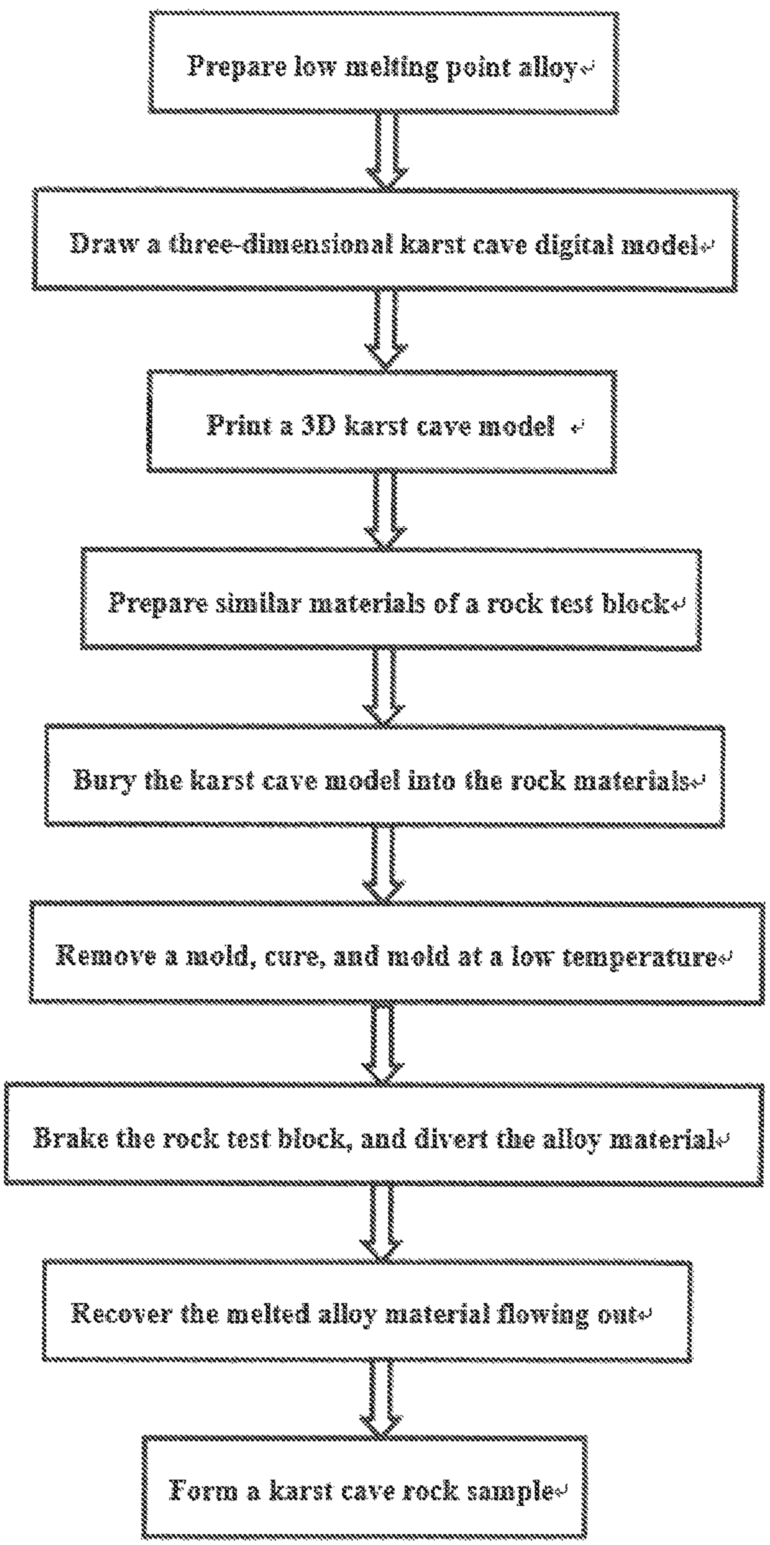
FIG. 1 is a flow diagram of a method for preparing a karst cave rock model.

Reference signs: 1 oven; 2 rock sample; 3 low-melting-point alloy recovery component; 4 diversion hole; 5 karst cave; 6 tunnel; 7 water-filling pressure device.

DETAILED DESCRIPTION OF THE EMBODIMENTS

The present invention will be further illustrated below in conjunction with the accompanying drawings and embodiments.

It should be pointed out that the following detailed descriptions are all exemplary and aim to further illustrate the present application. Unless otherwise specified, all technical and scientific terms used in the descriptions have the same meanings generally understood by those of ordinary skill in the art of the present application.

It should be noted that the terms used herein are merely for describing specific embodiments, but are not intended to limit exemplary embodiments according to the present application. As used herein, unless otherwise explicitly pointed out by the context, the singular form is also intended to include the plural form. In addition, it should also be understood that when the terms "include" and/or "comprise" are used in the specification, they indicate features, steps, operations, devices, components and/or their combinations.

As described in the background, the karst caves prepared in the present experiments of the prior art have the problems that the karst caves are not positioned accurately, the precision control on the dimensions of the karst caves is insufficient, the spatial shapes of the karst caves cannot be fully considered, the karst caves are prepared by hollowing rock test blocks after formation thereof, and the prepared karst caves are greatly different from the natural karst caves, etc. In order to solve the above technical problems, the present application proposes a method for preparing different types of karst caves based on 3D printing technology:

(1) preparing a low-melting-point alloy as a raw material for printing a karst cave;

(2) determining the size of a sample according to test requirements, drawing a three-dimensional karst cave digital model required by the experiment in advance in the three-dimensional mapping software based on a three-dimensional karst cave scanning result, and inputting the three-dimensional digital model into a 3D printer;

(3) printing a karst cave: melting low-melting-point alloy raw materials and then putting them into nozzles of the 3D printer respectively, and carrying out 3D printing to obtain a preliminary sample of the karst cave;

(4) determining a proportioning scheme of an aggregate and a cementing material of a rock model according to the geometric similarity ratio, strength similarity ratio, elastic modulus similarity ratio and the like of the rock sample and the model, the proportioning materials including standard sand, water, silicon powder, cement, a water reducer, etc.;

(5) weighing rock similar materials according to a proportion and uniformly mix them, pouring the mixture into a sample mold layer by layer while the karst cave model is buried into the mixture according to the position of the karst cave, with diversion holes being reserved, coating the interior of the mold with a release agent, and carrying out vibration molding;

(6) removing the mold, and curing the sample at a constant temperature and a constant humidity;

(7) molding a karst cave rock model at a low temperature;

(8) putting the molded test sample into an oven, and fully melting the karst cave made of the low-melting-point alloy at a constant temperature higher than 100° C. for more than 5 hours;

(9) diverting the melted alloy material out through diversion holes, and putting a tray under the diversion holes to recover the alloy material flowing out through vibration for use next time; and

(10) preparing a water-filled karst cave, wherein the diversion holes can be used as water filling holes to fill the karst cave with water, or a high-pressure water pump is used to continuously fill the karst cave with water through the diversion holes, to form a high-pressure water-rich karst cave.

Figure 2:
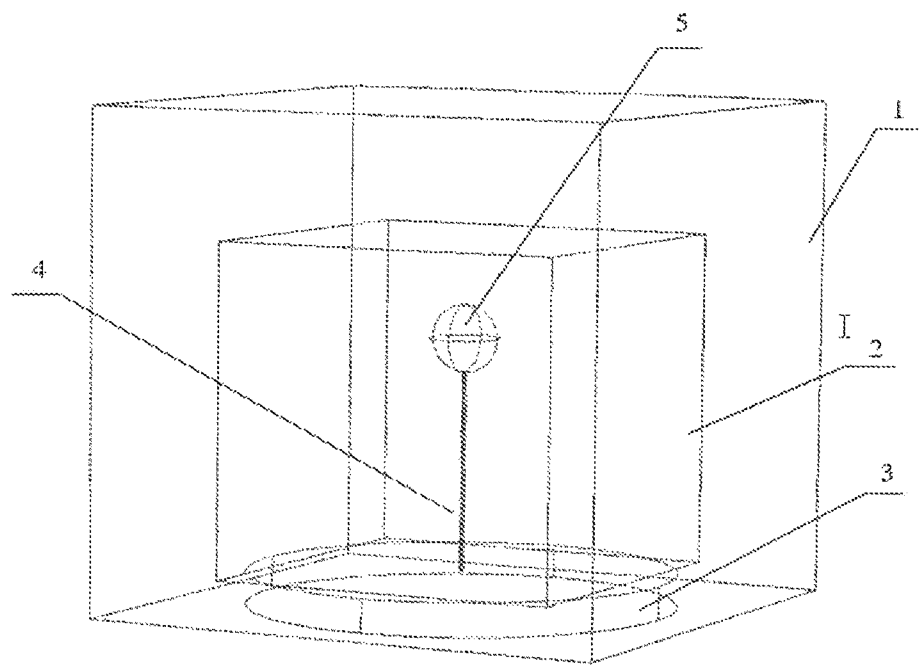
FIG. 2 is a schematic diagram of a baking guide device in the present invention.
Figure 3:
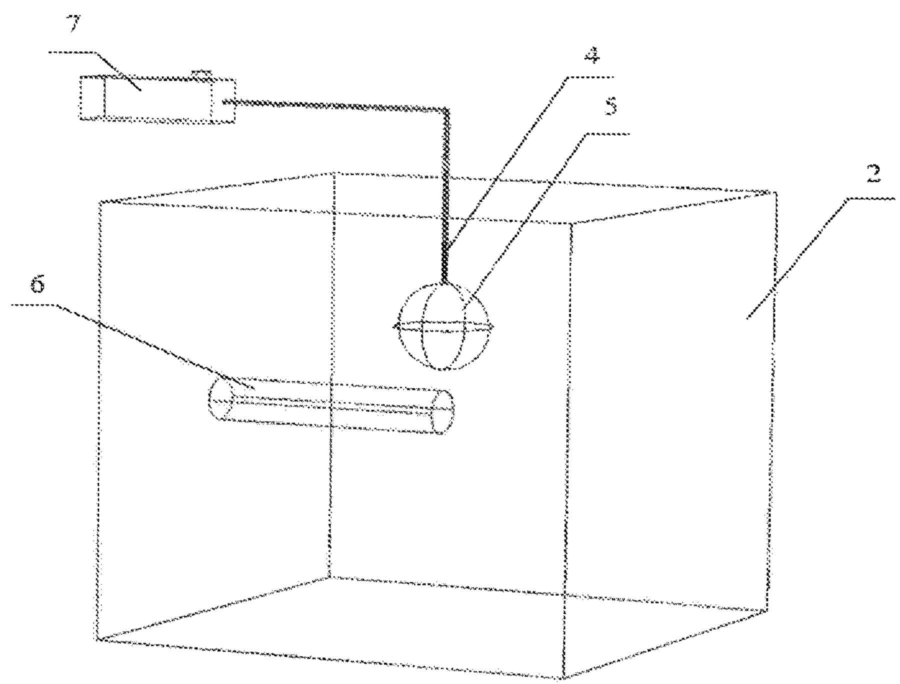
FIG. 3 is a schematic diagram of preparation of a water-filled karst cave.

In a typical embodiment of the present application, as shown in FIG. 1, the method specifically includes:

1. preparing a low-melting-point alloy as a raw material for printing a karst cave, where the specific method is as follows: a low-melting-point alloy is generally synthesized from low-melting-point metals such as Sn, Pb, Bi and Cd, and the alloy raw materials are prepared according to the proportion Sn:Pb:Bi:Cd=9.3:34.4:50.0:6.3;

2. determining the size of a sample according to test requirements, drawing a 3D karst cave digital model required by the experiment in advance in the 3D mapping software according to a geometric similarity ratio based on a 3D karst cave scanning result, and inputting the 3D digital model into a 3D printer, wherein the karst cave model may be drawn using CAD, SolidWorks or other software;

3. printing a karst cave: melting the above low-melting-point alloy raw materials into the nozzles of the 3D printer, and carrying out 3D printing to obtain a preliminary sample of the karst cave, wherein in order to save materials, the printed karst cave may be a hollow shell with certain deformation resistance, which can be filled with gravel mud particles as required;

4. determining a proportioning scheme of an aggregate and a cementing material of a rock model according to the geometric similarity ratio, strength similarity ratio, elastic modulus similarity ratio and the like of the rock sample and the model, the proportioning materials including standard sand, water, silicon powder, cement, a water reducer, etc., wherein the specific proportion is configured according to the actual rock properties of the project under study;

5. putting a mixture of rock similar materials into a mold and performing vibration molding as follows: weighing rock similar materials according to the proportion and uniformly mix them, pouring the mixture into a sample mold layer by layer while the karst cave model is buried into the mixture according to the position of the karst cave, with tiny diversion holes being reserved, coating the interior of the mold with a release agent, and carrying out vibration molding, wherein the diversion holes are obtained from pre-buried small low-melting-point alloy strips communicating with the karst cave and the outside, where after the alloy strips are melted, the alloy melt flows out to form the diversion holes, as shown in FIG. 2;

6. removing the mold, and curing the sample at a constant temperature and a constant humidity as follows: curing the sample together with the mold at room temperature for 30 hours to harden the rock similar materials, removing the mold, and curing the formed karst cave rock sample in a constant-temperature and constant-humidity curing box for 30 days at a curing temperature of 22° C. and a relative humidity of higher than 94%;

7. generating a karst cave: putting the molded test sample into an oven, and fully melting the karst cave made of the low-melting-point alloy and the alloy strips at a constant temperature higher than 100° C. for more than 5 hours, and putting a tray under the diversion holes of the sample during braking or electrified heating to recover the alloy material flowing out after the karst cave is melted, wherein after the alloy material has completely flowed out, a hollow karst cave is formed inside the rock test block;

8. filling gravel and preparing a muddy particle karst cave as follows: pouring fillings into the karst cave through an opening formed at the upper part when the karst cave is printed to one third in step 3, and continuously printing the karst cave till the printing is completed such that the fillings are sealed in the karst cave, wherein when the karst cave is generated in step 7, the low alloy material melts into liquid and flows out of the rock mass through the diversion holes, and the solid gravel and the muddy fillings cannot flow out through the small diversion holes, but are left in the formed karst cave cavity to form a filling type karst cave; and 9. preparing a water-filled karst cave as follows: filling the karst cave with water through the diversion holes by a high-pressure water pump after the preparation of the karst cave rock mass to obtain a water-filled karst cave with different water pressures, wherein the water filling pressure can be adjusted according to the experimental requirements.

Described above are merely preferred embodiments of the present application, and the present application is not limited thereto. Various modifications and variations may be made to the present application for those skilled in the art. Any modification, equivalent substitution, improvement or the like made within the spirit and principle of the present application shall fall into the protection scope of the present application.

Although the specific embodiments of the present invention are described above in combination with the accompanying drawings, the protection scope of the present invention is not limited thereto. It should be understood by those skilled in the art that various modifications or variations could be made by those skilled in the art based on the technical solution of the present invention without any creative effort, and these modifications or variations shall fall into the protection scope of the present invention.

The invention claimed is:

1. A method for preparing a karst cave based on 3D printing technology, comprising the following steps:

(1) determining the size of a sample according to test requirements, constructing a three-dimensional karst cave digital model based on a three-dimensional karst cave scanning result, and carrying out 3D printing by using an alloy to form a primary karst cave sample;

(2) determining a proportioning scheme of an aggregate and a cementing material of a rock model according to the geometric similarity ratio, strength similarity ratio and elastic modulus similarity ratio of the rock sample and the model, and preparing a rock similar material mixture according to the proportioning scheme;

(3) rock similar materials are weighed according to a proportion and uniformly mixed, the mixture is poured into a mold layer by layer while the karst cave model is buried into the mixture according to the position of a karst cave, with diversion holes being reserved; the interior of the mold is coated with a release agent, and vibration molding is carried out;

(4) curing the sample together with the mold at room temperature until the rock similar materials are hardened, removing the mold, curing the formed karst cave rock sample at a constant temperature and a constant humidity and then baking the same to form a rock sample with a hollow karst cave; and (5) filling the hollow karst cave with different fillings to form a different type of karst cave sample; the preparation method of the muddy particle karst cave is that, after the set portion is printed in the karst cave printing process, the printed portion has an opening through which the fillings are poured into the karst cave, and the karst cave is further printed till the printing is completed and the fillings are sealed in the karst cave, wherein preparing a water-filled karst cave is to fill the karst cave with water through the diversion holes after the preparation of the karst cave rock mass, and the water filling pressure is adjusted according to the experimental requirements to obtain a water-filled karst cave with different water pressures.

2. The method for preparing a karst cave based on 3D printing technology according to claim 1, wherein in step (1), the alloy comprises a low-melting-point metallic synthetic alloy having a melting point below 300° C.

3. The method for preparing a karst cave based on 3D printing technology according to claim 1, wherein in step (3), the diversion holes are obtained from pre-buried small low-melting-point alloy strips communicating with the karst cave and the outside, where after the alloy strips are melted, the alloy melt flows out to form the diversion holes.

4. The method for preparing a karst cave based on 3D printing technology according to claim 1, wherein in step (4), the sample is cured together with the mold at room temperature for a period of time until the rock similar materials are hardened; the mold is removed; and the formed karst cave rock sample is cured in a constant-temperature and constant-humidity curing box for a set time.

5. The method for preparing a karst cave based on 3D printing technology according to claim 1, wherein in step (4), the curing temperature is 20-25° C., and the curing relative humidity is higher than 94%.

6. The method for preparing a karst cave based on 3D printing technology according to claim 1, wherein in step (4), the formed test sample is baked or heated by electrifying a preset heating wire in the alloy; the karst cave made of the low-melting-point alloy and the alloy strips are fully melted; the alloy material flowing out after the karst cave is melted is recovered by virtue of the division holes of the sample during baking or electrified heating; and a rock test block with a hollow karst cave is obtained.

* * * * *